(12) United States Patent
Falco

(10) Patent No.: US 6,920,956 B1
(45) Date of Patent: Jul. 26, 2005

(54) DETECTABLE EARPLUG AND METHOD OF MANUFACTURE THEREOF

(75) Inventor: Robert N. Falco, Indianapolis, IN (US)

(73) Assignee: Cabot Safety Intermediate Corporation, Newark, DE (US)

( * ) Notice: Subject to any disclaimer, the term of this patent is extended or adjusted under 35 U.S.C. 154(b) by 740 days.

(21) Appl. No.: 09/226,467

(22) Filed: Jan. 7, 1999

(51) Int. Cl.⁷ ............................................. A61B 7/02
(52) U.S. Cl. ..................................................... 181/135
(58) Field of Search ................................ 181/129, 130, 181/135, 137; 2/209

(56) References Cited

U.S. PATENT DOCUMENTS

| | | |
|---|---|---|
| RE29,487 E | 12/1977 | Gardner, Jr. |
| 4,253,452 A | 3/1981 | Powers et al. |
| 4,533,356 A | 8/1985 | Bengmark et al. |
| 4,936,411 A | 6/1990 | Leonard |
| 5,044,463 A * | 9/1991 | Carr ........................... 181/135 |
| 5,203,352 A | 4/1993 | Gardner, Jr. |
| 5,420,381 A | 5/1995 | Gardner, Jr. et al. |
| 5,557,077 A | 9/1996 | Berg |
| 5,711,313 A | 1/1998 | Fleming |
| 5,792,998 A | 8/1998 | Gardner, Jr. et al. |
| 5,799,658 A | 9/1998 | Falco |

FOREIGN PATENT DOCUMENTS

| | | |
|---|---|---|
| EP | 0 244 979 | 11/1987 |
| EP | 0201348 A1 | 11/1992 |
| WO | WO 9218076 A | 10/1992 |

* cited by examiner

Primary Examiner—Khanh Dang
(74) Attorney, Agent, or Firm—Cantor Colburn, LLP

(57) ABSTRACT

An earplug including a foam body and a detectable insert completely encased by the foam body. The earplug is manufactured by forming a channel in the foam body and placing the detectable insert in the channel. The channel is formed by deforming the foam body using a punch. The foam body is made from a slow recovery foam which returns to its original shape thereby encapsulating the detectable insert within the foam body. In an alternative embodiment, the insert is projected into the foam body and the foam body recovers to encapsulate the insert.

2 Claims, 2 Drawing Sheets

DETECTABLE EARPLUG AND METHOD OF MANUFACTURE THEREOF

BACKGROUND OF THE INVENTION

The invention relates generally to foam earplugs and in particular to foam earplugs including a detectable insert encased by the foam earplug. Earplugs and other hearing protectors are worn by industrial workers to protect their hearing. When earplugs or other hearing protectors are worn in certain industries (e.g. food, beverage, pharmaceutical, tobacco, etc.), there is danger that an earplug may become intermixed with the product and cause contamination. To remedy this situation, there has been proposed providing a detectable insert in an earplug. U.S. Pat. Nos. 4,936,411 and 5,711,313 and European Patent Application 244979 disclose earplugs including a detectable component.

SUMMARY OF THE INVENTION

The present invention is an earplug including a foam body and a detectable insert completely encased by the foam body. The earplug is manufactured by forming a channel in the foam body and placing the detectable insert in the channel. The channel is formed by deforming the foam body using a punch or blade to open and separate the foam body. The foam body is made from a slow recovery foam which returns to its original shape thereby encapsulating the detectable insert within the foam body. In an alternative embodiment, the insert is projected into the foam body and the foam body recovers to encapsulate the insert.

The above-discussed and other features and advantages of the present invention will be appreciated and understood by those skilled in the art from the following detailed description and drawings.

BRIEF DESCRIPTION OF THE DRAWINGS

Referring now to the drawings wherein.

DETAILED DESCRIPTION OF THE PREFERRED EMBODIMENTS

Figure 1:
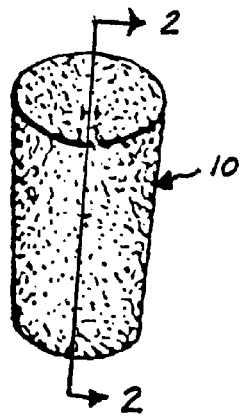
FIG. 1 is a perspective view of an earplug.
Figure 2:
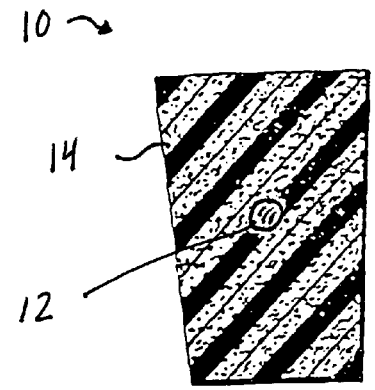
FIG. 2 is cross-sectional view taken along line 2—2 of FIG. 1.

FIG. 1 is a perspective view a detectable earplug in accordance with the present invention shown generally at 10. FIG. 2 is a cross-sectional view of the earplug 10 taken along line 2—2 of FIG. 1. The detectable earplug 10 includes a foam body 14 made from a slow recovery foam such as that disclosed in U.S. Patent Re 29,487, the entire contents of which are incorporated herein by reference, U.S. Pat. No. 5,203,352, the entire contents of which are incorporated herein by reference and U.S. Pat. No. 5,420,381, the entire contents of which are incorporated herein by reference. Encapsulated within foam body 14 is a detectable insert 12. Detectable insert 12 may be made from any detectable material including metal, magnetic material or x-ray detectable material. In an exemplary embodiment, insert 12 is spherical, has a 7/64" diameter and is made from 440 stainless steel. It is understood that other geometries may be used for insert 12. The insert 12 is sized so that it does not interfere with the rolling down of the foam body 14. In addition, the insert 12 does not interfere with attaching a cord to detectable earplug 10 as is known in the art. It is understood that detectable earplug 10 may include other non-foam components.

Figure 3:
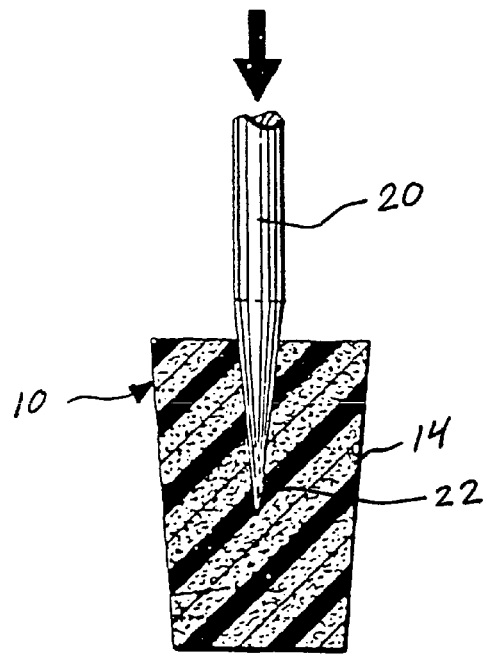
FIGS. 3–4 are cross-sectional views depicting a process of manufacturing the earplug of FIG. 1.
Figure 4:
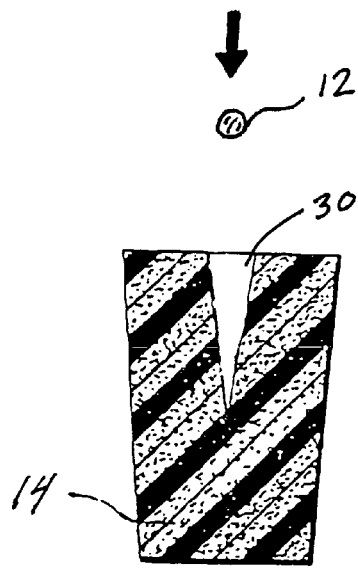

A method of manufacturing the earplug of FIG. 1 will be described with reference to FIGS. 3 and 4. As shown in FIG. 3, the first step is to create a channel in the foam body 14 using a punch or needle 20 which pierces through the foam body 14. Punch 20 is driven into foam body 14 until the tip 22 of the punch 20 is located approximately in the center of the earplug 10. Punch 20 compresses the foam body 14 to form a channel 30 shown in FIG. 4. In an exemplary embodiment, punch 20 is inserted along the central, longitudinal axis of the earplug 10. The depth of insertion of the punch 20 controls the location of the insert 12. The punch 20 is then removed leaving foam body 14 having a channel 30 formed therein as shown in FIG. 4. The channel 30 stays open and accessible due to the high hysteresis and slow recovery of the foam body 14. Insert 12 is then positioned in channel 30 as shown in FIG. 4. The foam body 14 then slowly recovers to encapsulate the insert 12 which results in the detectable earplug 10 as shown in FIG. 1. As a result, substantially the entire surface of the insert 12 in contact with foam body 14.

The process shown in FIGS. 3 and 4 may require that punch 20 remain in the foam body 14 for a predetermined period of time. As described in U.S. Pat. No. 4,352,452, the punch 20 may remain in the foam body 14 for a predetermined period of time (referred to as dwell time) so that channel 30 is adequately formed and does not close too rapidly. To eliminate the need for dwell time, one or both of the punch 20 or the foam body 14 may be chilled. Chilling the punch 20 or the foam body 14 increases the hysteresis of the foam which slows down the recovery of the foam. Accordingly, the punch 20 can be inserted into the foam body and removed rapidly and the channel 30 will remain open to allow insertion of the insert 12. There is no need for the punch 20 to remain in the foam body 14 for a predetermined period of time. This reduces cycle time of the manufacturing process and increases efficiency.

Figure 5:
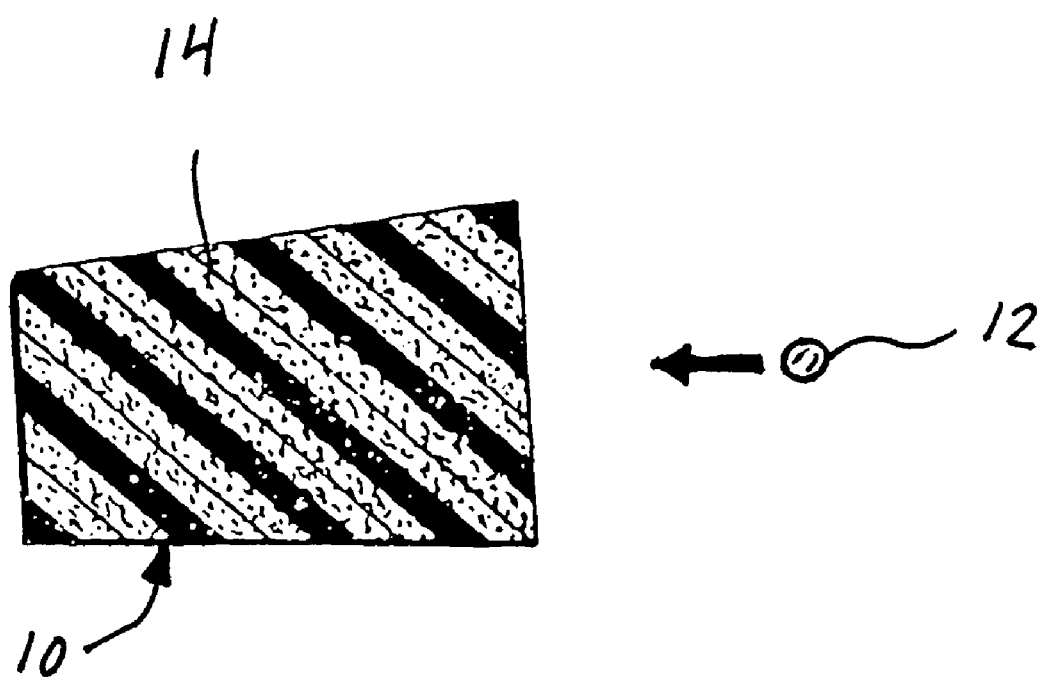
FIG. 5 is a cross-sectional view depicting an alternative process of manufacturing the earplug of FIG. 1.

FIG. 5 depicts an alternative method of manufacturing the earplug of FIG. 1. As shown in FIG. 5, the insert 12 is projected into the foam body 14 via a source of energy (e.g. compressed air). In the embodiment shown in FIG. 5, the insert is directed along the central, longitudinal axis of the foam body 14. The trajectory and speed of the insert 12 is controlled so that the insert 12 penetrates the foam body 14 and is lodged at a desired location as shown in FIG. 2. In an exemplary embodiment, the speed and trajectory of the insert 12 is controlled so that the insert comes to rest in the center of the earplug 10. The path formed by the insert 12 seals due to the recovery properties of the foam body 14.

Conventional detectable earplugs position the detectable portion on the outside of the earplug. In the present invention, the detectable insert is encapsulated within a foam body which improves the aesthetics of the earplug. In addition, the detectable insert in the present invention does not take up any of the outside surface area of the earplug. This allows the entire plug to function as intended.

The detectable earplug of the present invention includes a non-intrusive, encapsulated, detectable insert that does not interfere with the rolling down and insertion of the earplug or the ability to attach cords to the earplug. The insert is sized, shaped and positioned within the earplug so as to be unnoticeable to the wearer. The methods of manufacturing the earplug are efficient. The invention has been described with reference to a cylindrical earplug but it is understood that the detectable insert may be located in any shape earplug such as those disclosed in U.S. Pat. Nos. 4,461,290, 5,188,123, D371,193, D358.463, D307,636, D307,635, D307,325, and D303,014.

While preferred embodiments have been shown and described, various modifications and substitutions may be made thereto without departing from the spirit and scope of the invention. Accordingly, it is to be understood that the present invention has been described by way of illustration and not limitation.

What is claimed is:

1. A method of manufacturing an earplug comprising:
   providing an earplug having a foam body free of detectable material;
   forming a channel in said foam body;
   placing a detectable insert in said channel; and
   allowing said foam body to encapsulate said detectable insert so that said foam body completely surrounds said detectable insert, wherein said foam body is chilled.

2. A method of manufacturing an earplug comprising:
   providing an earplug having a foam body free of detectable material;
   forming a channel in said foam body;
   placing a detectable insert in said channel; and
   allowing said foam body to encapsulate said detectable insert so that said foam body completely surrounds said detectable insert, wherein said channel is formed by inserting a punch in said foam body and wherein said channel is formed by a punch and said punch is chilled.

* * * * *